United States Patent
Abadie et al.

(10) Patent No.: US 11,603,516 B2
(45) Date of Patent: Mar. 14, 2023

(54) DEVICE FOR MECHANICALLY CHARACTERIZING AN ELEMENT OF INTEREST SUCH AS AN OOCYTE

(71) Applicants: CENTRE NATIONAL DE LA RECHERCHE SCIENTIFIQUE, Paris (FR); UNIVERSITE DE FRANCHE-COMTE, Besancon (FR); ECOLE NATIONALE SUPERIEURE DE MECANIQUE ET DES MICROTECHNIQUES, Besancon (FR)

(72) Inventors: Joel Abadie, Besancon (FR); Racha Gana, Monastir (TN); Emmanuel Piat, Fontain (FR)

(73) Assignees: CENTRE NATIONAL DE LA RECHERCHE SCIENTIFIQUE, Paris (FR); UNIVERSITE DE FRANCHE-COMTE, Besancon (FR); ECOLE NATIONALE SUPERIEURE DE MECANIQUE ET DES MICROTECHNIQUES, Besancon (FR)

( * ) Notice: Subject to any disclaimer, the term of this patent is extended or adjusted under 35 U.S.C. 154(b) by 643 days.

(21) Appl. No.: 16/495,918

(22) PCT Filed: Mar. 20, 2018

(86) PCT No.: PCT/FR2018/050670
§ 371 (c)(1),
(2) Date: Sep. 20, 2019

(87) PCT Pub. No.: WO2018/172688
PCT Pub. Date: Sep. 27, 2018

(65) Prior Publication Data
US 2020/0131464 A1    Apr. 30, 2020

(30) Foreign Application Priority Data
Mar. 21, 2017   (FR) .................................. 1752330

(51) Int. Cl.
*G01N 3/42*       (2006.01)
*G01N 3/40*       (2006.01)
(Continued)

(52) U.S. Cl.
CPC ............ *C12M 35/06* (2013.01); *C12M 41/46* (2013.01); *G01N 3/42* (2013.01);
(Continued)

(58) Field of Classification Search
CPC .. G01L 1/005; G01L 1/04; G01B 7/16; G01B 3/002; G01N 2203/0075;
(Continued)

(56) References Cited

U.S. PATENT DOCUMENTS 4,611,487 A * 9/1986 Krenn ...................... G01N 3/42
                                                            73/81
4,959,552 A * 9/1990 Saffert ............... G01N 21/5911
                                                         250/559.26
(Continued)

FOREIGN PATENT DOCUMENTS

CN     1847847 A    10/2006
CN     1932511 A    3/2007
(Continued)

OTHER PUBLICATIONS

International Search Report, dated Jun. 7, 2018, from corresponding PCT application No. PCT/FR2018/050670.
(Continued)

*Primary Examiner* — Brandi N Hopkins
(74) *Attorney, Agent, or Firm* — Nixon & Vanderhye

(57) ABSTRACT

Disclosed is a device for mechanically characterizing an element of interest, for example an oocyte. The mechanical
(Continued)

characterization device includes: a support receiving a container suitable for containing a liquid medium; a holder for holding the element of interest; an indenting member; a magnet for generating a magnetic field in which the indenting member is intended to move and which participates in suspending the indenting member with an unstable horizontal direction oriented coaxially to the longitudinal axis; a controller to control the magnet to maneuver the indenting member in translation along the unstable horizontal direction; and a component for determining the mechanical characteristics of the element of interest.

16 Claims, 2 Drawing Sheets

(51) Int. Cl.
    *C12M 1/42*     (2006.01)
    *C12M 1/34*     (2006.01)

(52) U.S. Cl.
    CPC ........ *G01N 2203/0078* (2013.01); *G01N 2203/0085* (2013.01); *G01N 2203/0087* (2013.01); *G01N 2203/0089* (2013.01); *G01N 2203/0286* (2013.01)

(58) Field of Classification Search
    CPC .. G01N 2203/0286; G01N 3/46; G01N 11/10; G01N 11/16; G01N 33/5008; G01N 3/42; G01N 1/04; G01N 3/405; G01N 3/48; C12M 35/06; C12M 23/50; B01F 31/22; H02N 15/00; A61B 1/00158; C12N 13/00; G01R 1/10

See application file for complete search history.

(56) References Cited

U.S. PATENT DOCUMENTS

| | | | |
|---|---|---|---|
| 5,486,457 A | | 1/1996 | Butler et al. |
| 5,723,793 A | * | 3/1998 | Suzuki ............... G01L 1/005 73/789 |
| 2009/0068701 A1 | | 3/2009 | Elson et al. |
| 2011/0053241 A1 | | 3/2011 | Den Tooner et al. |
| 2014/0312251 A1 | | 10/2014 | Barbet |

FOREIGN PATENT DOCUMENTS

| | | |
|---|---|---|
| CN | 102759481 A | 10/2012 |
| WO | 2008/105919 A2 | 9/2008 |
| WO | 2017/020006 A1 | 2/2017 |

OTHER PUBLICATIONS

Guillou et al.; Dynamic monitoring of cell mechanical properties using profile microindentation; Scientific Reports; Feb. 9, 2016; pp. 1-13; vol. 6.

* cited by examiner

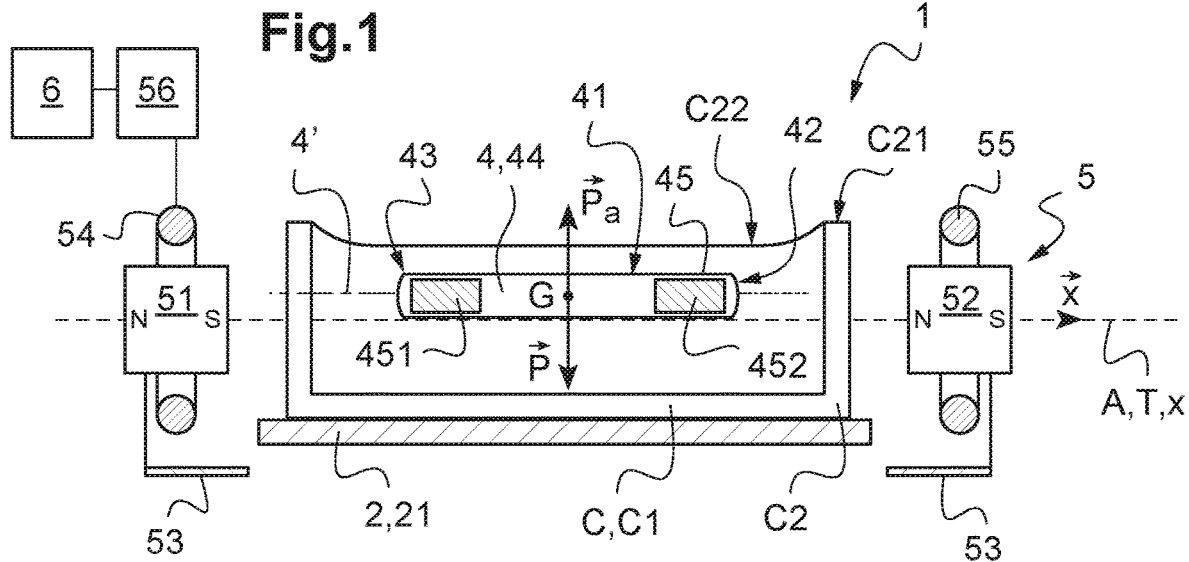
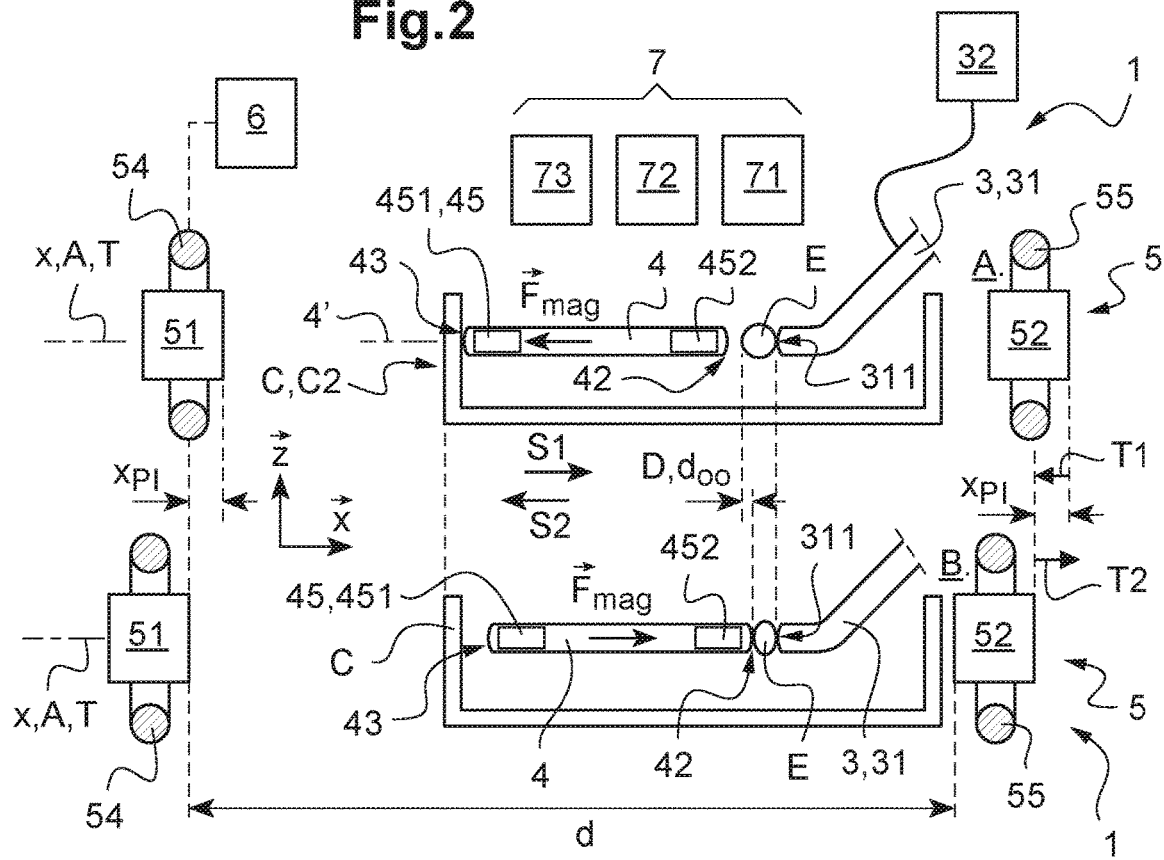

DEVICE FOR MECHANICALLY CHARACTERIZING AN ELEMENT OF INTEREST SUCH AS AN OOCYTE

TECHNICAL FIELD TO WHICH THE INVENTION RELATES

The present invention generally relates to the field of mechanical characterization of an element of interest.

It more particularly relates to a device suitable for mechanically characterizing a microscopic element of interest, possibly biological in nature, or even a cell, preferably an oocyte.

TECHNOLOGICAL BACK-GROUND

The mechanical characterization of an element of interest consists in analysing the intrinsic properties thereof (Young's modulus, Poisson's ratio, etc.), based on mechanical tests and trials.

Most of the current tests are intended to characterize metals and polymers at the macroscopic scale.

There are generally not suitable for characterizing the elements organic in nature, and even less at the microscopic scale.

Now, the mechanical characterization of living cells is a full problem, in particular in the field of medical assistance to procreation.

Indeed, such a mechanical characterization is probably a significant criterion to be taken into account during the selection of oocytes, in particular those having the ability to be fertilized.

New techniques have hence been specially developed for the mechanical characterization of living cells. These techniques generally consist in deforming the cell by applying to it a known load or stress, and to measure the deformation that results therefrom.

The most used techniques include micro-indentation and suction using a pipette.

But, in practice, these current techniques offer very limited possibilities of characterization.

There hence exists a need for a device that would allow a mechanical characterization by indentation to measure the forces applied on a microscopic element of interest (in particular a living cell), in an efficient, reliable and calibrated way.

OBJECT OF THE INVENTION

In this context, the present invention proposes a device for mechanically characterizing an element of interest, advantageously a microscopic element of interest, possibly biological in nature, or even a cell, preferably an oocyte.

More particularly, it is proposed according to the invention a mechanical characterization device that comprises:

support means, for receiving a container suitable for containing a liquid medium, holding means, for holding said element of interest in said liquid medium, an indenting member having a longitudinal axis and intended to remain in suspension in said liquid medium with said longitudinal axis oriented horizontally, wherein said indenting member includes at least one permanent magnet and one proximal end intended to indent said element of interest, magnetic means, for generating a magnetic field in which said indenting member is intended to move and which participates in the suspension of said indenting member with an unstable horizontal direction (advantageously oriented coaxially to said longitudinal axis), control means, intended to pilot said magnetic means so as to generate a variation of said magnetic field that is suitable for operating said indenting member in translation along said unstable horizontal direction, and means for determining the mechanical characteristics of said element of interest, taking into account the characteristics of said magnetic field and the value of translational displacement of said indenting member along said unstable horizontal direction when said proximal end of said indenting member generates a compression force on said element of interest.

In practice, the magnetic means allow applying a known load to the element of interest, through the indenting member.

For that purpose, this indenting member is held in a magnetic field intended to vary in a controlled manner.

The magnetic field implemented has then the following properties:

it preserves an unstable horizontal direction for the indenting member, it provides a stable holding of the indenting member, out of the measuring direction, and it acts as a negative-stiffness (or, as the case may be, positive-stiffness) magnetic spring on the indenting member along said unstable horizontal direction, to perform the load to the element of interest.

The stiffness of the magnetic spring is negative (or as the case may be positive) in the unstable horizontal direction; the element of interest then provides stability to the indenting member that compresses it.

The system is hence stabilized by the element of interest that is to be characterized, which provides optimum simplicity and efficiency.

With such technology, stiffnesses of the order of $10^{-3}$ N/m can be implemented, hence allowing the load to be controlled to within less than 10 nN, while providing an excellent linearity of measurement of the force applied.

Such a mechanical characterization device is moreover interesting for its low cost, robustness and easiness of implementation.

Other non-limitative and advantageous features of the mechanical characterization device according to the invention, taken individually or according to all the technically possible combinations, are the following:

the indenting member includes at least two permanent magnets that are arranged, on the one hand, with magnetic fields coaxial to each other and in a same direction NS-NS and, on the other hand, in a horizontal equilibrium position, in which the centre of buoyancy is intended to be merged with the centre of gravity; advantageously, the buoyancy produced by the liquid medium to the indenting member is equal, and opposite, to the weight of the indenting member;

said indenting member has the following features: a length comprised between 1 cm and 3 cm, a diameter comprised between 0.5 and 1.5 mm, and a mass comprised between 1 mg and 15 mg;

said indenting member comprises a body consisted of a capillary, for example made of glass, delimiting a sealed chamber that is filled with air and that contains said at least one permanent magnet;

the container comprises a bottom connected to a lateral wall, a free upper edge of which delimits an upper opening, for example a Petri dish;

the magnetic means comprise at least two permanent magnets that are arranged coaxially, along a horizontal axis, and in the same direction NS-NS, and means for operating said permanent magnets in translation; preferably, said at least two permanent magnets are each arranged within an electromagnetic coil, wherein said electromagnetic coils are arranged coaxially along the horizontal axis and are connected to means for piloting the electric current powering said electromagnetic coils; said at least two permanent magnets, and, as the case may be, said at least two electromagnetic coils, are advantageously arranged on either side of the container, at a constant distance d from each other; for example, the operating means consist of micro-translation plates;

the holding means comprise a suction pipette;

the means for determining the mechanical characteristics of said element of interest comprise means for determining the value of translational displacement of the indenting member along said unstable horizontal direction; these determination means advantageously comprise optical means, suitable for capturing images comprising the element of interest cooperating with the proximal end of the indenting member, and means for analysing said captured images, suitable for determining the value of the translational displacement of said indenting member along said unstable horizontal direction;

the support means comprise means for heating said container.

The invention also proposes a medically assisted procreation injection station, equipped with a device according to the invention.

The invention also relates to a method for studying the mechanical characteristics of an element of interest, advantageously a microscopic element of interest, possibly biological in nature, or even a cell, preferably an oocyte, by implementing a device according to the invention.

This method comprises:

a) a preparation phase during which, on the one hand, said element of interest is held in the liquid medium of the container by said holding means and, on the other hand, the magnetic means generate an initial magnetic field that allows holding said indenting member in an initial position at rest, remote from said element of interest, b) a loading phase during which the magnetic means are piloted so as to modify (possibly progressively) the magnetic field from said initial magnetic field to a modified magnetic field (advantageously constant or evolving; for example, by translationally operating the magnetic means and/or by piloting the electric current injected into the electromagnetic coils) to operate said indenting member in translation along said unstable horizontal direction, in a loading direction in which said proximal end of said indenting member generates a compression force to said element of interest held by said holding means, c) an unloading phase during which the magnetic means are piloted so as to restore (advantageously progressively) said initial magnetic field in which said indenting member is operated in translation along said unstable horizontal direction, in an unloading direction in which said proximal end of said indenting member moves apart from said element of interest held by said holding means, said method comprises a step of collecting the value of translational displacement of said indenting member along said unstable horizontal direction, at least during the loading phase, and said method comprises a step of determining mechanical characteristics of said element of interest, taking into account the value of translational displacement of said indenting member along said unstable horizontal direction and the characteristics of said magnetic field (i.e., as the case may be, the value of electric current injected into the electromagnetic coils and/or the value of displacement of the magnetic means).

Preferably, the loading and unloading steps are performed at a very low speed comprised between 0.1 and 50 micrometres per second.

DETAILED DESCRIPTION OF AN EXEMPLARY EMBODIMENT

The following description in relation with the appended drawings, given by way of non-limitative example, will allow a good understanding of what the invention consists of and of how it can be implemented.

In the appended drawings:

FIG. 1 is a general and schematic view of a part of the mechanical characterization device according to the invention;

FIG. 2 shows the main steps of the method to study the mechanical characteristics of an element of interest, advantageously an oocyte, by implementing the mechanical characterization device according to FIG. 1, with in particular a preparation phase (FIG. 2, part A) and a loading phase (FIG. 2, part B);

MECHANICAL CHARACTERIZATION DEVICE

Figure 3:
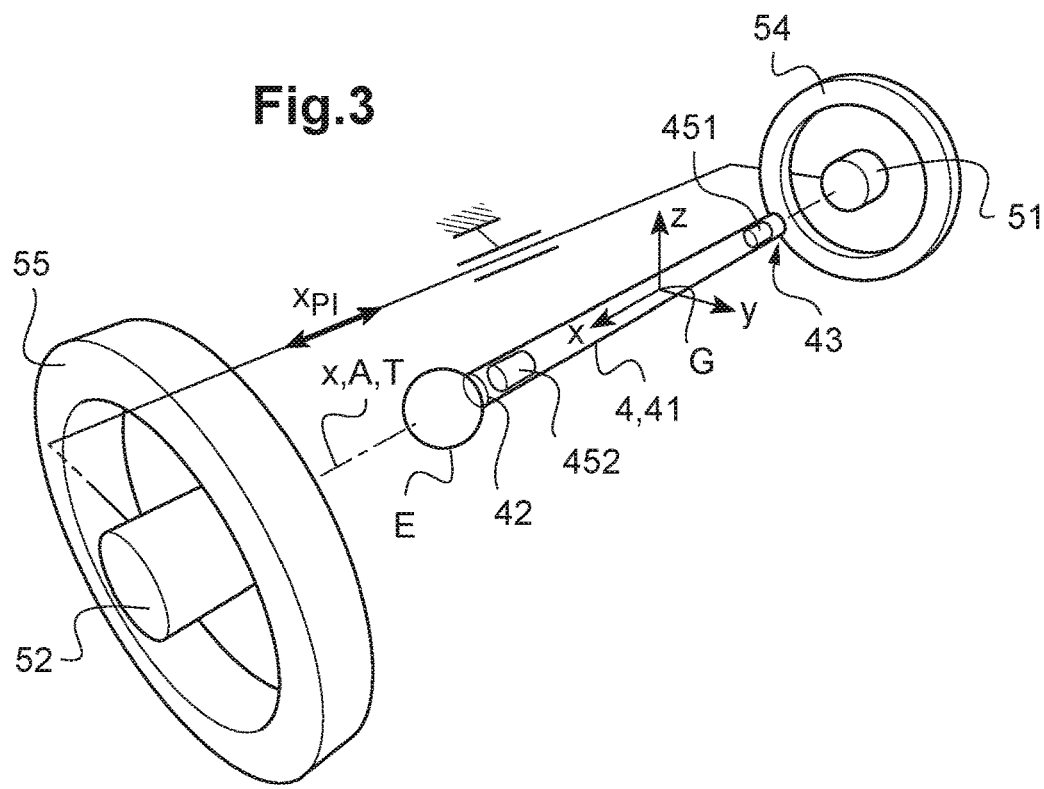
FIG. 3 is a general and schematic perspective view of the mechanical characterization device according to FIGS. 1 and 2 (for the sake of simplification, the support means and the holding means are not shown in this FIG. 3)

The device 1 according to the invention, shown in FIGS. 1 and 2, consists of a device 1 for mechanically characterizing an element of interest.

By "mechanical characterization", it is meant the analysis of the intrinsic mechanical properties of the element of interest, from mechanical tests and trials.

The mechanical characterization device 1 according to the invention is intended in particular to allow determining the mechanical response of the element of interest.

It allows in particular establishing the evolution of the compression distance D (for example in μm) as a function of the compression force (indentation) $\hat{F}_E$ (for example in nN), during an operation of indentation (load/unload) on this element of interest (as illustrated by the Example described hereinafter in relation with FIG. 4).

For that purpose, according to the invention, the mechanical characterization device 1 has a magnetic nanoforce sensor, which is based on the use of a passive magnetic spring and on the use of the unstable direction of this passive magnetic spring to perform the mechanical characterization measurements.

By "magnetic spring", it is meant a device comprising a magnet held in stable equilibrium by restoring forces stemming from remote actions and for which there is no dry friction disturbing the movement of the magnet. These actions are equivalent to those produced by a non-materialized spring whose ends are connected, on the one hand, to that magnet and, on the other hand, to a fixed point of reference.

A so-called "passive" magnetic spring provides stability to the indentation device, without addition of energy nor feedback control.

In this mechanical characterization device 1, the measurement is performed in a magnetic unstable horizontal direction x and using the repulsive reaction of the element of interest E to stabilize the direction of measurement.

For that purpose, as shown in FIGS. 1 and 2, the mechanical characterization device 1 comprises:

support means 2, for receiving a container C suitable for containing a liquid medium, holding means 3, for holding the element of interest E in the liquid medium, an indenting member 4 (transducer of the sensor), having a longitudinal axis 4' and intended to remain in suspension in the liquid medium with said longitudinal axis 4' oriented horizontally, magnetic means 5, for generating a magnetic field in which said indenting member 4 is intended to move, which participate to the suspension of said indenting member 4 and define an unstable horizontal direction x (materialized by the reference axis $\vec{x}$ in the FIGS. 1 to 3), control means 6, for controlling the operation of the indenting member 4 in translation along the unstable horizontal direction, and determination means 7, for determining the mechanical characteristics of the element of interest E.

Generally, for the sake of simplification, the above-mentioned unstable horizontal direction and reference axis are sometimes denoted by a same reference $\vec{x}$.

Support Means

The support means 2 are conventional per se, for example as a plate.

These support means 2 advantageously include means 21 for heating the container C, for example as a thermal plate.

For its part, the container C comprises a bottom C1 connected to a lateral wall C2, a free upper edge C21 of which delimits an upper opening C22.

Such a container C hence advantageously consists of a Petri dish, made of glass or plastic.

The liquid medium, for its part, advantageously consists of an aqueous medium, adapted to the element of interest.

For example, in the case of an oocyte, the aqueous medium advantageously consists of an embryo culture medium which is conventional per se.

Holding Means

As shown in FIG. 2, the holding means 3 are suitable for holding the element of interest E in the liquid medium (not shown).

These holding means 3 herein comprise a suction pipette 31, whose free end 311 is intended to dive into the liquid medium.

This free end 311 advantageously defines a vertical surface intended to extend perpendicularly to the unstable horizontal direction $\vec{x}$.

The suction pipette 31 is also associated with suction means 32, suitable for providing the gripping force for gripping the element of interest E at the free end 311 thereof.

Indenting Member

The indenting member 4 is intended, on the one hand, to remain in suspension in the liquid medium, with its longitudinal axis 4' oriented horizontally and, on the other hand, to be subjected to a magnetic force capable of moving it in the unstable horizontal direction x (materialized by the horizontal axis of reference $\vec{x}$ in FIGS. 1 to 3).

Preferably, in practice, the longitudinal axis 4' of the indenting member 4 is intended to be oriented coaxially (or at least parallel) about the unstable horizontal direction x and of the horizontal axis of reference $\vec{x}$.

Herein, the indenting member 4 comprises a body 41 that has an elongated and cylindrical shape.

The body 41 has two ends, located on the longitudinal axis 4', i.e. a proximal end 42 intended to indent the element of interest E and an opposite, distal end 43.

The shape of the proximal end 42 is adapted to the test performed and to the shape of the element of interest E studied.

This body 41 is formed by a capillary, for example made of glass, delimiting a sealed chamber 44 filled with air. This characteristic participates to the suspension of the indenting member 4 in the liquid medium.

Preferably, the manufacturing of the indenting member 4 allows having a buoyancy $\vec{P}a$ equal (or at least almost equal), and opposite, to the weight $\vec{P}$ thereof.

The indenting member 4 hence remains caught at a constant, or at least approximately constant, altitude about the horizontal axis of reference $\vec{x}$.

The indenting member 4 also includes at least one permanent magnet 45 (internal), to participate, on the one hand, to the suspension in the liquid medium and, on the other hand, to hold its longitudinal axis 4' coaxial (or at least parallel) to the horizontal axis of reference $\vec{x}$.

By "permanent magnet", it is meant a ferromagnetic body that produces and sustains a magnetic field without intervention of an electric current. The permanent magnet consists for example of a neodymium-iron-boron magnet. Such a permanent magnet has conventionally North (N) and South (S) poles.

More precisely, said at least one permanent magnet 45 allows the indenting member 4 to act as a system connected to a passive magnetic spring.

Herein, the body 41 of the indenting member 4 contains two permanent magnets 451, 452 (for example, cylindrical) that are arranged within the sealed chamber 44.

The permanent magnets 451, 452 are arranged with coaxial magnetic fields and in a same direction NS-NS.

In other words, the permanent magnets 451, 452 are herein arranged coaxially relative to each other and with respect to the longitudinal axis 4' of the indenting member 4. Moreover, the South pole of one of the permanent magnets 451, 452 is located opposite the North pole of the other of the permanent magnets 451, 452.

The permanent magnets 451, 452 are also arranged according to a horizontal equilibrium position, in which the centre of buoyancy is intended to be merged (or at least almost merged) with the centre of gravity G of the indenting member 4.

Only by way of indication and without being in any way limitative, the indenting member 4 has the following characteristics:

a length (distance between the two ends 42, 43 of its body 41) comprised between 1 cm and 3 cm, a diameter (cross-section perpendicular to the longitudinal axis 4') comprised between 0.5 and 1.5 mm, and a mass comprised between 1 mg and 15 mg.

Magnetic Means

The magnetic means 5, coupled to the indenting member 4, are designed to form a passive magnetic spring.

For that purpose, the magnetic means 5 generate a magnetic field in with the indenting member 4 is intended to move. This magnetic field participates to the suspension, guiding and orientation of this indenting member 4 along the unstable horizontal direction x.

In particular, the magnetic means 5 are able to generate, along the directions $\vec{y}$ and $\vec{z}$, very low restoring forces that hold the indenting member 4 in equilibrium (in position and orientation) about the horizontal axis of reference $\vec{x}$.

It will be noted that the directions y and z are directions perpendicular to the unstable horizontal direction x, oriented horizontally and vertically, respectively.

These magnetic means 5 are moreover intended to exert a controlled magnetic force $\vec{F}_{mag}$ on the indenting member 4, oriented coaxially to the unstable horizontal direction x (FIG. 2).

The magnetic force $\vec{F}_{mag}$ conditions the displacements and the equilibrium of the indenting member 4 along the unstable horizontal direction x.

Herein, this unstable magnetic force $\vec{F}_{mag}$ corresponds to the resultant of the magnetic force brought to the centre of gravity G of the indenting member 4.

For that purpose, the magnetic means 5 herein comprise two permanent magnets 51, 52 (external), of the cylindrical type for example, which are arranged coaxially, along a horizontal axis A and in the same direction NS-NS.

The horizontal axis A of these two permanent magnets 51, 52 is merged with the horizontal axis of reference $\vec{x}$. In other words, the magnetization of the permanent magnets 51, 52 is coaxial to the horizontal axis A.

The horizontal axis A of these two permanent magnets 51, 52 hence defines the horizontal axis of reference $\vec{x}$ and the unstable horizontal direction x.

The permanent magnets 51, 52 are arranged on either side of the container C, at a constant distance d with respect to each other.

The two permanent magnets 51, 52 are herein each arranged within an electromagnetic coil 54, 55.

The two electromagnetic coils 54, 55 are arranged coaxially with respect to the above-mentioned horizontal axis A of the two associated permanent magnets 51, 52.

These two electromagnetic coils 54, 55 are advantageously wired in series and oriented SN-NS.

Hence, the two permanent magnets 51, 52, and the two electromagnetic coils 54, 55 are arranged on either side of the container C, at a constant distance d with respect to each other.

The magnetic means 5 also comprise means 53 for the operation in translation of these two permanent magnets 51, 52, and of the associated electromagnetic coils 54, 55, along a horizontal direction T that is oriented coaxially to the horizontal axis A.

This horizontal direction T is hence coaxial, or at least parallel, to the unstable horizontal direction x.

This operation in translation along the horizontal direction T of the two permanent magnets 51, 52, and of the electromagnetic coils 54, 55, is intended to be performed over a controlled and determined distance $x_{PI}$ (FIG. 2).

For example, these operating means 53 consist of microtranslation plates.

The magnetic means 5 also comprise means 56 for piloting the electric current powering the electromagnetic coils 54, 55, so as to generate a variation of the magnetic field intended to perform (or at least to participate to) a translational operation of the indenting member 4 along the unstable horizontal direction x.

For example, these piloting means 56 consist of an electric power circuit, conventional per se, suitable for generating an electric current of a determined value in the electromagnetic coils 54, 55.

Control Means

The control means 6 are intended to pilot the magnetic means 5 so as to generate a variation of the magnetic field. This magnetic field variation then performs a translational operation of the indenting member 4, along the unstable horizontal direction $\vec{x}$.

These control means 6 advantageously consist in a control part of an industrial programmable automaton system. They comprise in particular a computer program including program code means intended to be executed by a computer.

These control means 6 are in particular designed to pilot herein:

the means 53 for translationally operating these two permanent magnets 51, 52 and the associated electromagnetic coils 54, 55, and/or the means 56 for piloting the electric current applied to the electromagnetic boils 54, 55.

As mentioned hereinabove, the translational operation of the two permanent magnets 51, 52 and of the associated electromagnetic coils 54, 55, along to the horizontal direction T, is advantageously performed over a controlled and determined distance $x_{PI}$ (FIG. 2).

Determination Means

The determination means 7 are configured to determine the mechanical characteristics of the element of interest E, taking into account:

the characteristics of the magnetic field generated by the magnetic means 5 (for example, the stiffness constant of the magnetic spring) and the value D of translational displacement of the indenting member 4 along the unstable horizontal direction x, when the indenting member 4 generates a compression force on the element of interest E (FIG. 2, part B).

The determination means 7 comprise means 71, 72 for determining the value D of translation displacement of the indenting member 4 along the unstable horizontal direction x.

To determine this displacement value D, the determination means 7 comprise for example optical means 71, suitable for capturing images comprising the element of interest E cooperating with the proximal end 42 of the indenting member 4 (FIG. 2, part B).

These optical means 71 comprise for example a camera/tube/lens system, placed above the container C.

These optical means 71 allow following the deformations of the element of interest E, but also calculating by automated image processing the positions of the indenting member 4.

Still to determine this displacement value D, the determination means 7 also advantageously comprise analysis means 72 that are suitable for determining, from images captured by the optical means 71, the value D of translation displacement of the indenting member 4 along the unstable horizontal direction x.

In other words, this displacement value D corresponds to the distance between, on the one hand, an initial position $x_i^{init}$ of the indenting member 4 and, on the other hand, a final position $x_i^{max}$ of the indenting member 4 (advantageously caused by the displacement $x_{PI}$ of the permanent magnets 51, 52 and of the two electromagnetic coils 54, 55 of the magnetic means 5 and/or by the current injected into the two associated electromagnetic coils 54, 55).

Generally, this value D is also denoted $d_{oo}$ in the case of an element of interest of the oocyte type.

The analysis means 72 also advantageously comprise a computer program of the image analysis software type, including program code means intended to be executed by a computer.

These program code means use for example an image processing algorithm, based on the normalized cross-correlation (NCC) method.

In practice, the load applied to the element of interest E is modulated from the measurement of the displacement value D (also called "compression distance"), from the control of the distance $x_{PI}$ of translational operation of the two permanent magnets 51, 52 and/or from the current injected into the associated electromagnetic boils 54, 55.

The determination means 7 also comprise calculation means 73 (for example, a computer program) that are configured to determine, from the above-mentioned collected data, the mechanical characteristics of the element of interest E.

These mechanical characteristics advantageously comprise a curve showing the evolution of the displacement value D (compression) as a function of the value of the force $\hat{F}_E$ (effort applied by the element of interest E to the indenting member 4), during an indenting process (in loading, or even also in unloading) on this element of interest E.

A maximum compression distance $D^{max}$ (to be applied to the element of interest for a given test) may be fixed (predetermined).

The force $\hat{F}_E^{max}$ is the value of the force $\hat{F}_E$ that is obtained for:

a displacement of the external permanent magnets 51, 52 over the predetermine distance $x_{PI}$ and/or a predetermined value of current injected into the two associated electromagnetic coils 54, 55.

The particularity of this device is that the instability of the indenting member 4 along the horizontal axis of reference x is avoided by creating an effort equal, and opposite, to the unstable magnetic force $\hat{F}_{mag}$ by placing the element of interest E (for example the oocyte) opposite the indenting member 4.

At equilibrium, we will hence have:

$$\hat{F}_{mag} + \hat{F}_E = 0$$

where $\hat{F}_E$ (also called $\hat{F}_{oo}$ for an oocyte) is the effort applied by the element of interest E to the indenting member 4.

The relative clearance to be applied between the indenting member 4 and the external permanent magnets 51, 52 and/or the current injected into the two associated electromagnetic coils 54, 55 will be each located in a determined range.

During an ideal loading, it is tried to maintain a constant and low-amplitude speed for the indenting member 4.

In such conditions:

$$\hat{F}_E = K(x_i - x_i^{init} - x_{PI} + x_{PI}^{init}) + K_{elec} I$$

with $\hat{F}_E$, the force applied to an element of interest (in N),

K, the stiffness of the magnetic spring (obtained for example from simulations made with the real parameters of the device) in N/m;

$x_{PI}$, the displacement applied to the permanent magnets 51, 52 of the magnetic means 5, $x_i$, all the positions of the indenting member, $K_{elec}$, the electrical stiffness of the electromagnetic coils 54, 55 (in N/A), I, the current injected in the electromagnetic coils 54, 55 (in A), these electromagnetic coils 54, 55 being wired in series and directed SN-NS, $x_{PI}^{init}$ and $x_i^{init}$, the initial positions of the permanent magnets 51, 52, and electromagnetic coils 54, 55 belonging to the magnetic means 5 and of the indenting member 4, respectively.

For its part, the compression distance $D^{max}$ is the value of the compression distance D, obtained for a displacement over the maximum predetermined distance $x_{PI}$ and/or a predetermined maximum current I.

This compression distance D of the element of interest E (denoted "$d_{oo}$" in the case of an element of interest of the oocyte type) is given by the following formula:

$$D = U_{\frac{pixel}{m}} (x_{px} - x_{px}^{init})$$

wherein:

$U_{\frac{pixel}{m}}$ is the conversion gain between the displacement measurements provided by the vision system (in pixel) and the real displacements of the indenting member 4 (in m), $x_{px}$, all the positions of the indenting member 4 measured in pixel, and $x_{px}^{init}$, the initial position of the indenting member 4 measured in pixel.

Figure 4:
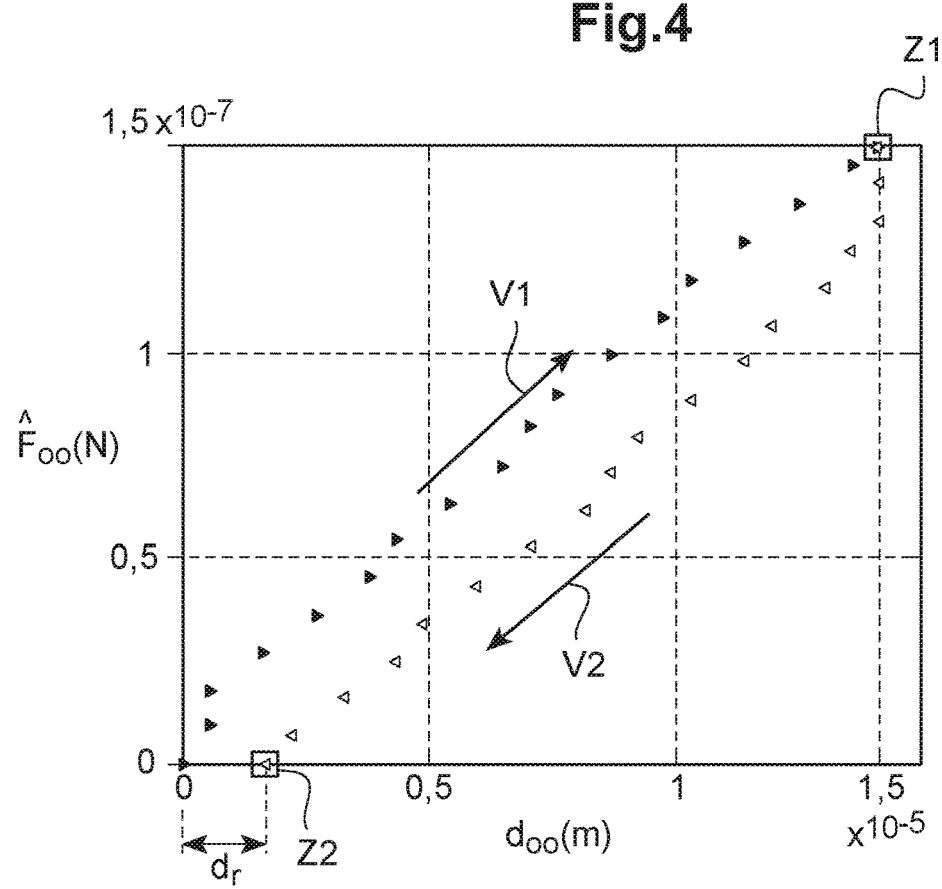
FIG. 4 shows an example of mechanical response of an oocyte, measured during the method according to FIG. 2 (ordinate: force in Newton; abscissa: value of translational displacement of the indenting member in the loading phase then in the unloading phase).

Based on these values, the determination means 7 can plot a curve of mechanical response of the element of interest (see for example FIG. 4).

Generally, the compression distance D could be measured through any suitable means, other than optical means.

Method for Studying the Mechanical Characteristics of an Element of Interest

The implementation of the mechanical characterization device 1 is described hereinafter in relation with FIG. 2. This method of implementation comprises the following successive phases.

Firstly, this method is initiated by a preparation phase (FIG. 2, part A), during which the element of interest E is positioned and held in the liquid medium of the container C, by the holding means 3.

Herein, the element of interest E is held by suction using the holding pipette 31.

Generally, the indenting member 4, coupled to the magnetic means 5, straddles, midwater, in the liquid medium of the container C.

In this configuration, the indenting member 4 is subjected to magnetic forces through the permanent magnets 51, 52 of the magnetic means 5. The current I injected in the electromagnetic coils 54, 55 is null.

Still in this configuration, the indenting member 4 is stable in the horizontal y and vertical z directions perpendicular to its longitudinal axis 4'.

On the other hand, the indenting member 4 is unstable in the unstable horizontal direction x directed coaxially to said longitudinal axis 4'. The measurement of the force is then intended to be performed along this unstable horizontal direction x.

During this preparation phase, the magnetic means 5 generate an initial magnetic field P1 that allows holding the indenting member 4 in an initial position at rest, remote from the element of interest E.

More precisely, an unstable magnetic force $\hat{F}_{mag}$ (directed to the left in FIG. 2) is exerted, which tends to move apart the indenting member 4 with respect to the element of interest E.

The distal end 43 of the indenting member 4 is then held in contact with the lateral wall C2 of the container C; the proximal end 42 of the indenting member 4 is located remote from the element of interest E (for example, a few tens of micrometres).

The preparation phase is followed with a phase of instability tilting (the proximal end 42 comes into contact with the element of interest E without applying any effort to the latter $\hat{F}_E=0$).

The indenting member 4 loses the contact with the container C when the modulus of the unstable magnetic force $\hat{F}_{mag}$ becomes higher to the adhesion force between the indenting member 4 and the container C.

The operating means 53 are used to adjust the position of the magnets 51 and 52 and to guarantee $\hat{F}_E=0$ when the indenting member 4 is in contact with the element of interest E just before the beginning of the loading phase.

The method is continued with the loading phase during which the indenting member 4 is operated in translation so that its proximal end 42 generates a compression force to the element of interest E carried by the holding means 3 (FIG. 2, part B).

For that purpose, the magnetic means 5 are piloted so as to modify the magnetic field, from the initial magnetic field P1 to a modified magnetic field P2 (constant or evolving), wherein the indenting member 4 is operated in translation along the unstable horizontal direction x, in a loading direction S1.

Herein, the modification of the magnetic field, from the initial magnetic field P1 to the modified magnetic field P2, is obtained:

by translationally operating the two permanent magnets 51, 52, along the horizontal T and in a first direction T1 (to the left in FIG. 2), and/or by applying a controlled and determined current I to the electromagnetic coils 54, 55.

As the case may be, the translational operation of the two permanent magnets 51, 52, along the horizontal T, is performed over the controlled and determined distance $x_{PI}$.

In practice, this loading step is advantageously performed at a very low speed of the indenting member 4 (almost-static loading), for example comprised between 0.1 and 50 micrometres per second.

The modulus of the force $\hat{F}_E$ applied to the element of interest E is then advantageously equal to the modulus of the unstable magnetic force $\hat{F}_{mag}$.

In practice, the load applied to the element of interest E is hence modulated based on the control:

of the distance $x_{PI}$ of translational operation of the two permanent magnets 51, 52, and/or of the current I applied to the electromagnetic coils 54, 55.

Following this loading phase, an unloading phase is implemented, during which the proximal end 42 of the indenting member 4 is moved apart from the element of interest E that is still held by the holding means 3 (passage from FIG. 2, part B to FIG. 2, part A).

For that purpose, the magnetic means 5 are piloted to as to come back to the initial magnetic field P1 in which the indenting member 4 is operated in translation along the unstable horizontal direction x, in an unloading direction S2.

Herein, the return to the initial magnetic field P1 is obtained:

by a translational operation (return) of the two permanent magnets 51, 52 over the distance $x_{PI}$, along the direction T and in a second direction T2 (opposite to the first direction T1), and/or by cancelling the value of the current I applied to the electromagnetic coils 54, 55.

During this method, the determination means 7 perform a step of collecting the value D of translational displacement of the indenting member 4 along the unstable horizontal direction x and, as the case may be, the value of the current I applied to the electromagnetic coils 54, 55.

This collection step is implemented during the loading phase, and advantageously also during the unloading phase.

Based on the collected data, the determination means 7 perform a step of determining the mechanical characteristics of the element of interest E, also called step of visualization of the mechanical response of the element of interest E.

As described hereinabove, this determination (or visualization) step takes advantageously into account the characteristics of the magnetic field (in particular the stiffness constant K and $K_{elec}$), the value D of translational displacement of the indenting member 4 along the unstable horizontal direction x and the value of the electric current I injected into the electromagnetic coils 54, 55.

The data obtained may be for example in the form of a characteristic curve of the mechanical response of the element of interest E measured during a load/unload test at constant speed.

This curve shows for example the correlation between, on the one hand, the value of the force applied to the element of interest and, on the other hand, the value of the distance of compression of said element of interest by the indenting member.

Such a curve is illustrated for example in FIG. 4 for an element of interest E consisting of a human oocyte.

Field of Application

The determination device 1 according to the invention is hence adapted to the mechanical characterization of an element of interest E.

By "element of interest", it is advantageously meant an element of interest having a microscopic size, i.e. an element having a size lower than 1 mm, preferably between 10 μm and 1 mm.

This microscopic element of interest is advantageously biological in nature, i.e. for example a cell, preferably an oocyte.

A "cell" is the structured unit constitutive of any living being, formed of a cytoplasm surrounded with a membrane and liable to contain a nucleus.

By "oocyte", it is meant the female sexual cell of the metazoans, preferably a human oocyte.

In this case, the components used, which are in contact with the oocyte and its culture medium, are advantageously non-gametotoxic and for single use only.

Hence, the mechanical characterization device 1 is perfectly adapted to equip a medically assisted procreation injection station.

Such a station conventionally includes a holding syringe, an injection syringe and an inverted microscope.

More generally, this determination device 1 according to the invention may be interesting in the fields of application in which it is interesting to measure mechanical characteristics of any type of cells.

The following fields may be mentioned:
the field of reproduction, and of gametes in the wide sense (human and animal);
the study of cancer cells (measuring characteristics of a cancer cell allows, inter alia, measuring if this cell is invasive);
the veterinary field;
the bacteriological field;
the field of zoology and unicellular world;
the field of botany;
the field of nanotribology.

EXAMPLE

Material

An example of a characterization device 1 is described hereinafter.

The permanent magnets 51, 52 of the magnetic means 5 have a diameter and a length equal to 10 mm and a load density equal to 1.25 A/m².

They are arranged horizontally, along the axis x, so as to respect the magnetic configuration N-S N-S along their longitudinal axis (axis x) and separated by a distance d equal to 10.4 cm.

The indenting member 4 includes the two permanent magnets 45, of length equal to 1 mm and diameter equal to 0.5 mm, placed horizontally. Their magnetization is also horizontal, oriented along the axis x and in the same direction. It is equal to $3.10^5$ A/m.

The distance between the two permanent magnets 45 of the indenting member 4 is equal to 1.5 cm.

The centre of gravity G of the indenting member 4 is defined at the centre of the segment separating the permanent magnets 45.

The direction z represents the vertical of the indenting member 4, direction for which the weight is exerted.

Stiffness of the Magnetic Spring

To perform measurements on the oocytes, the force range to be applied is comprised between 0 and about 1 μN.

The relative clearance to be applied between the indenting member 4 and the external permanent magnets 51, 52 will be located in the range [−2 mm, 2 mm].

Indeed, if $G^x = 2$ mm then $F_{max}^x = 2.6$ μN.

Such an effort allows applying a load to all the human oocytes within the framework of medical assistance to procreation.

A curve, for which an affine function has been superimposed in the interval [−2 mm, 2 mm], allows validating the linearity of $F_{max}^x$ as a function of $G^x$:

$$F_{max}^x = K \cdot G^x$$

with K, the stiffness of the magnetic spring along the direction x.

In the configuration retained, the stiffness of the magnetic spring is equal to 0.0013 N/m. It is a very low value with respect, for example, to the stiffness of the lever of an atomic force microscope whose most flexible levers are about ten times stiffer.

Result

FIG. 4 shows the mechanical response of an immature oocyte.

The oocyte has a diameter equal to 144 μm and a cytoplasm diameter of 106 μm.

The curve of evolution of the force $\hat{F}_{oo}$ illustrates the loading phase (upper part −V1).

During this phase, the oocyte is compressed by the indenting member until reaching a compression distance $d_{oo}^{max}$ equal to 14 μm, which corresponds to the maximum deformation of the oocyte for a force $\hat{F}_{oo}^{max}$ of 150 nN (square Z1 in FIG. 4).

The lower part of the curve (V2) shows the unloading phase. It corresponds to the moving back of the indenting member up to the square Z2 of FIG. 4.

This curve highlights a hysteresis, due to the viscous nature of the oocyte. A residual deformation ($d_r$) of the oocyte is observable at the end of the unloading.

The invention claimed is:
1. A device for mechanically characterizing an element of interest (E), advantageously a microscopic element of interest, possibly biological in nature, or even a cell,
wherein the mechanical characterization device (1) comprises:
support means (2), for receiving a container (C) suitable for containing a liquid medium,
holding means (3), for holding said element of interest (E) in said liquid medium,
an indenting member (4) having a longitudinal axis (4') and intended to remain in suspension in said liquid medium, midwater, with said longitudinal axis (4') oriented horizontally, wherein said indenting member (4) includes at least one permanent magnet (45) and one proximal end (42) intended to indent said element of interest (E),
magnetic means (5), for generating a magnetic field in which said indenting member (4) is intended to move and which participates in the suspension of said indenting member (4) midwater in the liquid medium of the container (C), and wherein said indenting member (4) is unstable in an unstable horizontal direction (x) directed coaxially to said longitudinal axis (4') of said indenting member (4),
control means (6), intended to pilot said magnetic means (5) so as to generate a variation of said magnetic field that is adapted to operate said indenting member (4) in translation along said unstable horizontal direction (x), and means (7) for determining the mechanical characteristics of said element of interest (E), taking into account the characteristics of said magnetic field and the value (D) of translational displacement of said indenting member (4) along said unstable horizontal direction (x) when said proximal end (42) of said indenting member (4) generates a compression force to said element of interest (E).

2. The device for mechanically characterizing an element of interest (E) according to claim 1, wherein the indenting member (4) includes at least two permanent magnets (45) that are arranged:

with magnetic fields coaxial to each other and in a same direction NS-NS, and in a horizontal equilibrium position, in which the centre of buoyancy is intended to be merged with the centre of gravity.

3. The device for mechanically characterizing an element of interest (E) according to claim 1, wherein said indenting member (4) comprises a body (41) consisted of a capillary delimiting a sealed chamber (44) that is filled with air and that contains said at least one permanent magnet (45).

4. The device for mechanically characterizing an element of interest (E) according to claim 1, wherein the container (C) comprises a bottom (C1) connected to a lateral wall (C2), a free upper edge (C21) of which delimits an upper opening (C22), for example a Petri dish.

5. The device for mechanically characterizing an element of interest (E) according to claim 1, wherein the magnetic means (5) comprise:

at least two permanent magnets (51, 52) that are arranged coaxially, along a horizontal axis (A), and in the same direction NS-NS, and means (53) for operating said permanent magnets (51, 52) in translation.

6. The device for mechanically characterizing an element of interest (E) according to claim 5, wherein said at least two permanent magnets (51, 52) are each arranged within an electromagnetic coil (54, 55), wherein said electromagnetic coils (54, 55) are arranged coaxially along the horizontal axis (A) and are connected to means (56) for piloting the electric current powering said electromagnetic coils (54, 55).

7. The device for mechanically characterizing an element of interest (E) according to claim 5, wherein said at least two permanent magnets (51, 52), and said at least two electromagnetic coils (54, 55), are arranged on either side of the container (C), at a constant distance d from each other.

8. The device for mechanically characterizing an element of interest (E) according to claim 1, wherein the holding means (3) comprise a suction pipette (31).

9. The device for mechanically characterizing an element of interest (E) according to claim 1, wherein the means (7) for determining the mechanical characteristics of said element of interest (E) comprise means (71, 72) for determining the value (D) of translational displacement of the indenting member (4) along said unstable horizontal direction (x).

10. A medically assisted procreation injection station, equipped with a device according to claim 1.

11. A method for studying the mechanical characteristics of an element of interest (E) by implementing a device (1) according to claim 1, wherein the method comprises:

a) a preparation phase in which, on the one hand, said element of interest (E) is held in the liquid medium of the container (C) by said holding means (3) and, on the other hand, the magnetic means (5) generate an initial magnetic field (P1) that allows holding said indenting member (4) in an initial position at rest, remote from said element of interest (E) and midwater in the liquid medium of the container (C), b) a loading phase during which the magnetic means (5) are piloted so as to modify the magnetic field from said initial magnetic field (P1) to a modified magnetic field (P2), wherein said indenting member (4) is operated in translation along said unstable horizontal direction (x), in a loading direction in which said proximal end (42) of said indenting member (4), midwater in the liquid medium of the container (C), generates a compression force to said element of interest (E) held by said holding means (3), c) an unloading phase during which the magnetic means (5) are piloted so as to restore said initial magnetic field (P1) in which said indenting member (4) is operated in translation along said unstable horizontal direction (x), in an unloading direction in which said proximal end (42) of said indenting member (4), midwater in the liquid medium of the container (C), moves apart from said element of interest (E) held by said holding means (3), said method comprises a step of collecting the value (D) of translational displacement of said indenting member (4) along said unstable horizontal direction (x), at least during the loading phase, and said method comprises a step of determining mechanical characteristics of said element of interest (E), taking into account the characteristics of said magnetic field (E) and the value (D) of translational displacement of said indenting member (4) along said unstable horizontal direction (x).

12. The method according to claim 11, wherein the magnetic means (5) comprise:

at least two permanent magnets (51, 52) that are arranged coaxially, along a horizontal axis (A), and in the same direction NS-NS, and means (53) for operating said permanent magnets (51, 52) in translation;

wherein the characteristics of said magnetic field are function of:

the value of displacement of the magnetic means (5) and/or the value of the electric current injected into the electromagnetic coils (54, 55).

13. The method according to claim 12, wherein the element of interest (E) is a cell chosen among:

the oocytes, or the cancer cell.

14. The method according to claim 11, wherein the element of interest (E) is a cell chosen among:

the oocytes, or the cancer cell.

15. The method according to claim 11, wherein the magnetic means (5) comprise:

at least two permanent magnets (51, 52) that are arranged coaxially, along a horizontal axis (A), and in the same direction NS-NS; and means (53) for operating said permanent magnets (51, 52) in translation;

wherein said at least two permanent magnets (51, 52) are each arranged within an electromagnetic coil (54, 55), wherein said electromagnetic coils (54, 55) are arranged coaxially along the horizontal axis (A) and are connected to means (56) for piloting the electric current powering said electromagnetic coils (54, 55), and wherein the characteristics of said magnetic field are function of:

the value of displacement of the magnetic means (5) and/or the value of the electric current injected into the electromagnetic coils (54, 55).

16. The method according to claim 15, wherein the element of interest (E) is a cell chosen among:

the oocytes, or the cancer cell.

* * * * *